(12) United States Patent
Ruben

(10) Patent No.: US 8,141,556 B2
(45) Date of Patent: Mar. 27, 2012

(54) METALLIZATION WITH TAILORABLE COEFFICIENT OF THERMAL EXPANSION

(75) Inventor: David A. Ruben, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 1369 days.

(21) Appl. No.: 11/741,593

(22) Filed: Apr. 27, 2007

(65) Prior Publication Data

US 2008/0269623 A1 Oct. 30, 2008

(51) Int. Cl.
*A61B 19/00* (2006.01)

(52) U.S. Cl. ........................................................ 128/897

(58) Field of Classification Search ................... 128/897, 128/898, 899
See application file for complete search history.

(56) References Cited

U.S. PATENT DOCUMENTS

| | | | |
|---|---|---|---|
| 2,564,706 A * | 8/1951 | Mochel | 338/308 |
| 3,114,066 A * | 12/1963 | Allen et al. | 313/509 |
| 3,465,279 A * | 9/1969 | Krehbiel | 439/161 |
| 7,148,577 B2 * | 12/2006 | Jones | 257/782 |

FOREIGN PATENT DOCUMENTS

| WO | 03041096 A | 5/2003 |
|---|---|---|
| WO | 2006104432 A | 10/2006 |

OTHER PUBLICATIONS

International Search Report, PCT/US2008/061738, Oct. 24, 2008, 7 Pages.
Arshak et al., "Development of oxide thick film capacitors for a real time pressure monitoring system", Materials Science and Engineering C, Elsevier Science S.A., CH, vol. 27, No. 5-8 (Jul. 17, 2006), pp. 1406-1410.
Srikanth et al., "Thermal expansion anisotropy, microcracking and acoustic emission of Nb2O5 ceramics", Ceramics International, Elsevier, NL, vol. 18, No. 4, (Jan. 1, 1992), pp. 251-261.
Douglass et al., "The thermal expansion of niobium pentoxide and its effect on the spalling of niobium oxidation films", Journal of the Less-Common Metals, Elsevier-Sequoia, CH, vol. 5, No. 2, (Apr. 1, 1963), pp. 151-157.

* cited by examiner

*Primary Examiner* — Samuel Gilbert
(74) *Attorney, Agent, or Firm* — Carol F. Barry

(57) ABSTRACT

The present invention is directed to an interconnect for an implantable medical device. The interconnect includes a pad and a first layer introduced over the pad. At least one of the pad or the first layer comprise a negative coefficient of thermal expansion (CTE) material.

10 Claims, 6 Drawing Sheets

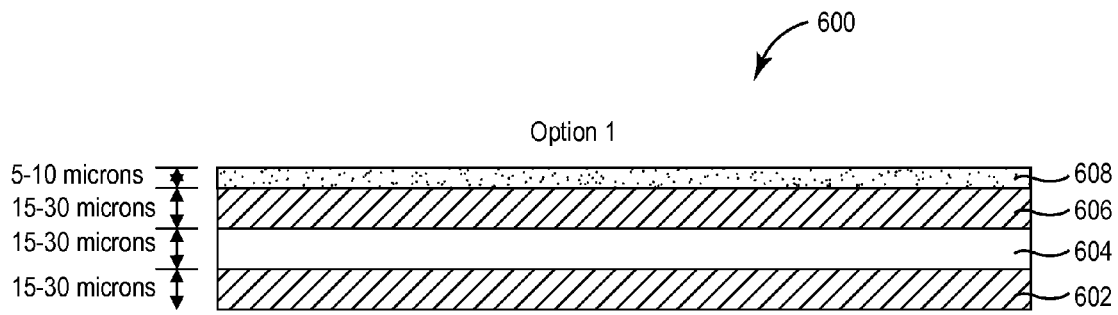
Fig. 11
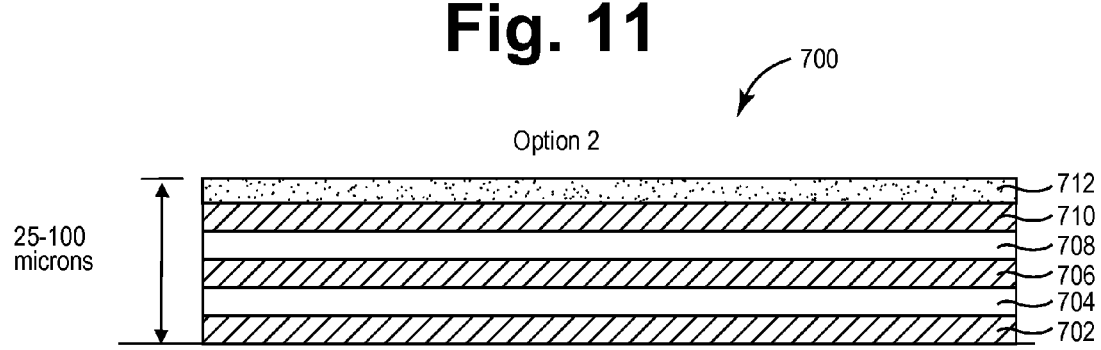
Fig. 12
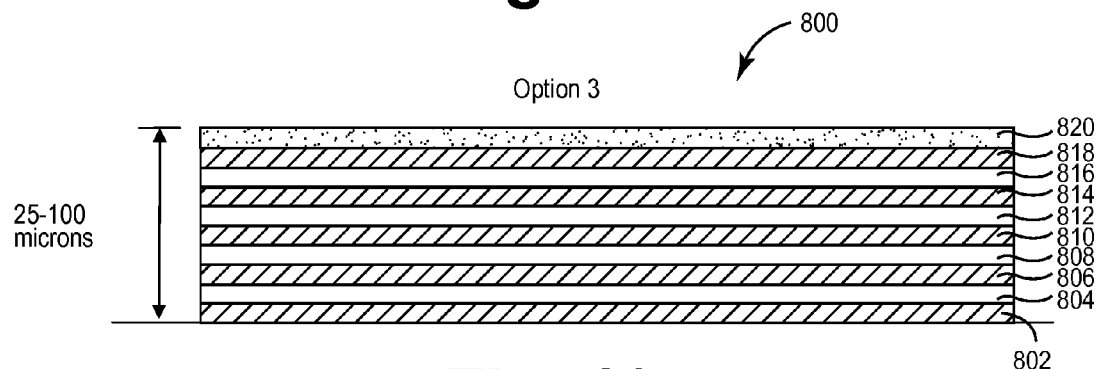
Fig. 13
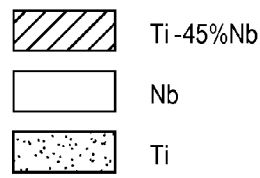

US 8,141,556 B2

METALLIZATION WITH TAILORABLE COEFFICIENT OF THERMAL EXPANSION

BACKGROUND

Many of the embodiments in this disclosure relate generally to medical devices, and, more particularly, implantable medical devices (IMDs).

Blood pressure monitoring may be used to assist a medical practitioner in diagnosing cardiovascular and other conditions of a patient. In many instances, blood pressure is monitored indirectly since this technique is relatively non-invasive and is useful for obtaining an approximate blood pressure measurement. In some circumstances, however, a more accurate blood pressure measurement may be needed. In such case, direct blood pressure monitoring, utilizing a device that is surgically implanted into a patient's bloodstream, may be employed.

Some direct pressure monitoring device configurations may include a capsule having a pressure transducer disposed therein. The capsule may include an opening that allows fluid to contact the pressure transducer directly. When the device is appropriately deployed within the patient, blood that is pumped by the heart may exert pressure against the pressure transducer. The pressure transducer may, in turn, sense the exerted pressure and communicate a signal representative of the sensed pressure to a pressure measurement gauge or other appropriate pressure-measuring device.

Such pressure monitoring devices may have disadvantages. For example, because the pressure transducer directly contacts the patient's blood, it may be more susceptible to corrosion. Thus, in cases in which the pressure transducer includes an integrated circuit chip, the device may degrade over time. Furthermore, blood may coagulate around the capsule opening, which may, in turn, affect pressure transducer operation. As a result, there may be difficulties associated with using such pressure monitoring devices for long-term pressure monitoring in an implant environment.

Some pressure monitoring devices may encase a pressure transducer (e.g., a MEMS/IC-type pressure transducer) within a fluid-filled, smooth-surfaced capsule and rigidly attach the pressure transducer to the capsule. In such devices, the pressure transducer is hermetically sealed, and thus not exposed to external media, such as biological fluids. The capsule may include a flexible diaphragm disposed over an opening. When pressure is exerted on the diaphragm, the pressure may be transferred to the pressure transducer via the internal fluid. The pressure transducer may communicate with, e.g., an IMD via a pressure monitoring lead. When such devices are disposed within a patient's heart chamber, heart contractions may cause force to be applied to the lead, thereby applying force directly to the rigidly attached pressure transducer. This strain may decrease the structural integrity of the pressure-monitoring device over time.

Other transducers used in other environments may experience similar issues. Such transducers may include sensing transducers, actuating transducers, IC-only transducers, or combinations thereof, or other suitable transducers.

BRIEF DESCRIPTION OF THE FIGURES

FIG. 11 is a cross-sectional view of an exemplary layered interconnect between a conductor and a sensor.
FIG. 12 is a cross-sectional view of another exemplary layered interconnect between a conductor and a sensor.
FIG. 13 is a cross-sectional view of yet another exemplary layered interconnect between a conductor and a sensor.

DETAILED DESCRIPTION OF ILLUSTRATIVE EMBODIMENTS

The following detailed description of illustrative embodiments should be read with reference to the drawings, in which like elements in different drawings are numbered identically. The drawings depict illustrative embodiments and are not intended to limit the scope of the invention. Rather, the present invention is defined solely by the claims.

In one embodiment, the invention includes a transducer module. The transducer module may include a transducer, which may include an electrically conductive interface pad. The transducer may be configured to provide an electrical signal to the interface pad. The transducer module may include a media-exposed interconnect. The media-exposed interconnect may be generally exposed when in an implant environment. The media-exposed interconnect may include at least one conductive layer deposited over the interface pad. The media-exposed interconnect may be coupled to a conductor to provide a conductive interface between the transducer and the conductor.

In another embodiment, the invention includes a method for creating a robust, media-exposed interconnect to connect a transducer with an implantable medical device. The method may include providing a transducer that includes an electrically-conductive interface pad. The interface pad may be configured to provide an electrical communication interface for the transducer. The method may include depositing a first layer over the pad. The first layer may be selected from the group consisting of titanium, niobium, tantalum, vanadium, hafnium, zirconium, and alloys thereof. The method may include attaching a conductor to the pad. The conductor may be configured to communicate electrically with the implantable medical device.

Embodiments of the present invention may have one or more of the following advantages. Some embodiments may be manufactured easier and/or at a reduced cost relative to the prior art. Some embodiments may provide for increased durability/longevity. For example, some embodiments may provide for a more durable interconnect between a sensor or actuator transducer and a conductor. In such embodiments, the interconnect may provide continuous electrical communication when the sensor or actuator transducer is subjected to a DC bias. Some embodiments may be smaller than the prior art, resulting in valuable space savings. Some embodiments may have increased bio-stability and/or bio-compatibility.

Figure 1:
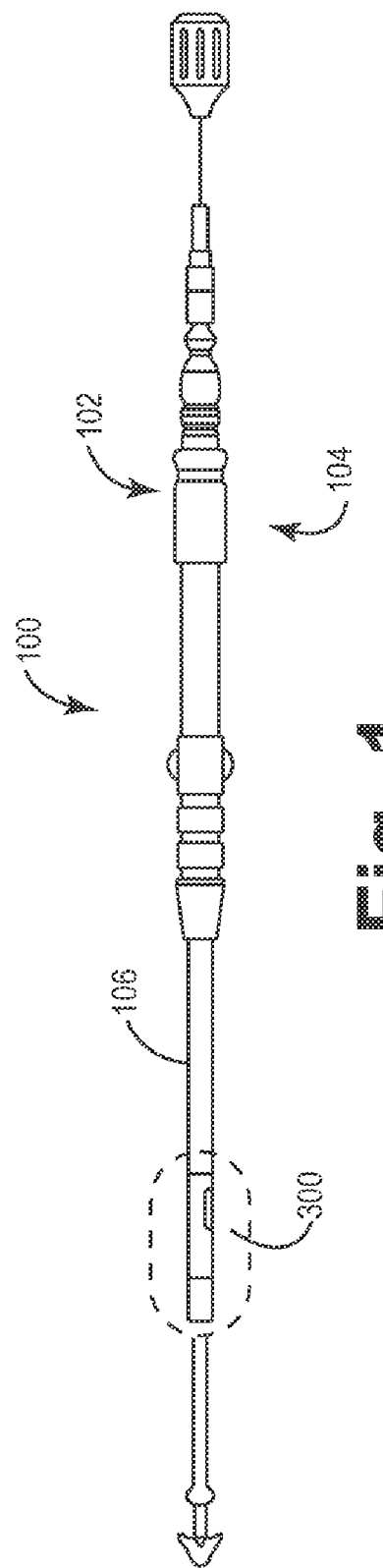
FIG. 1 is a side view of an exemplary lead.

FIG. 1 is a side view of an exemplary medical lead 100, which may be configured to be coupled to an IMD or other monitoring device. The lead 100 may include a transducer module 300. The lead 100 may be any one of a number of different types of leads. For example, the lead 100 may be a pressure monitoring lead, a therapy lead, or other known types of leads. The lead 100 may include a connector assembly 102, a lead body 106, and transducer module 300. The connector assembly 102 may be located at a proximal section 104 of the lead 100 and may be configured to be coupled to an IMD to electrically couple the lead 100 thereto.

Figure 2:
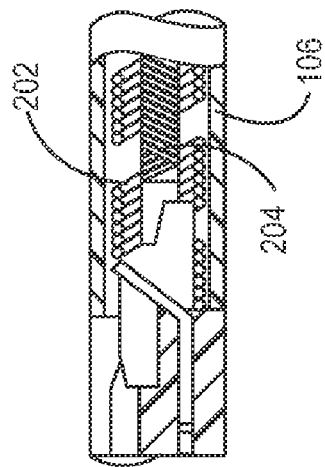
FIG. 2 is a cross sectional view of a portion of an exemplary lead body that may be implemented within the lead depicted in FIG. 1.

FIG. 2 is a cross-sectional view of an exemplary portion of the lead body 106. The lead body 106 may include wire coils 202 and 204. The wire coils 202 and 204 may be configured to electrically couple the connector assembly 102 to the transducer module 300. The wire coils 202 and 204 are each depicted herein as single pole coiled wire conductors, but any suitable electrical configuration for coupling connector assembly 102 and transducer module 300 may be employed. Furthermore, the wire coils 202 and 204 may be made of any suitable biocompatible material such as titanium or the like.

Figure 3:
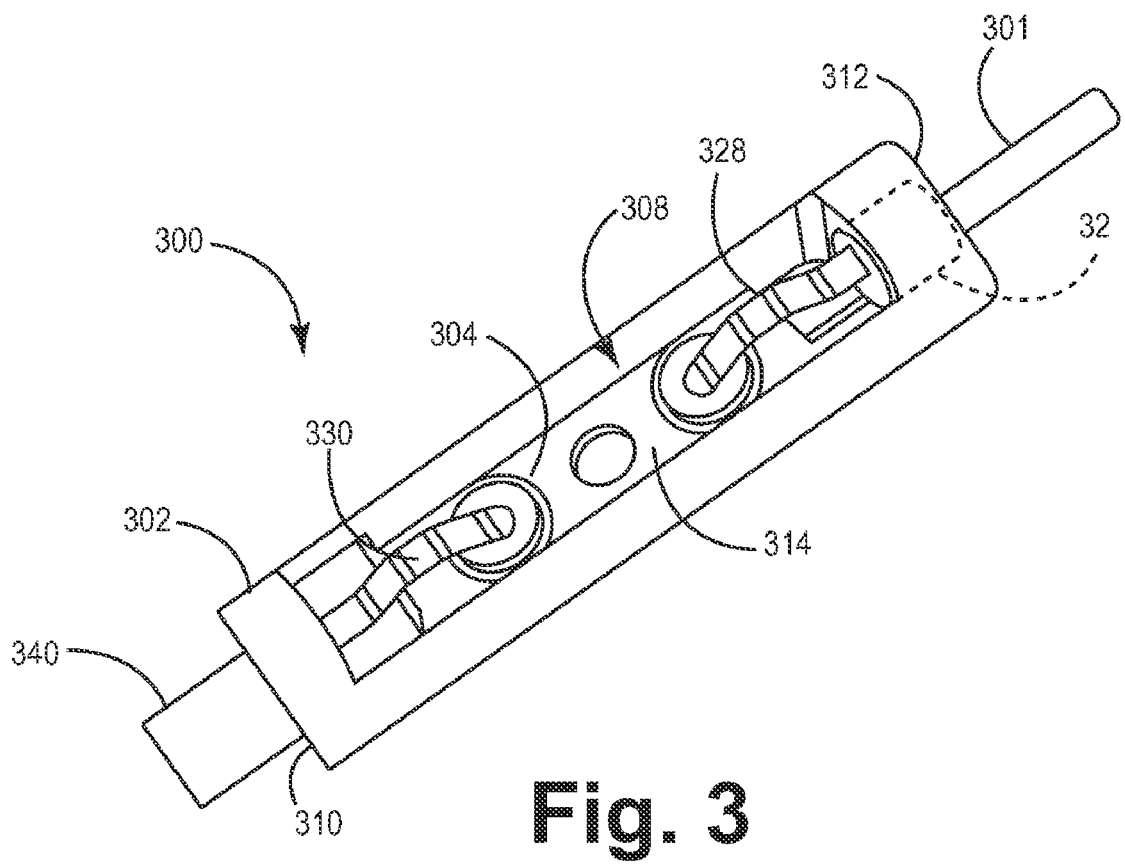
FIG. 3 is a perspective view of an exemplary transducer module that may be implemented within the lead depicted in FIG. 1.

FIG. 3 shows a transducer module 300, which may be configured to, e.g., sense blood pressure exerted thereon by a patient's blood flowing therearound. The transducer module 300 may include feedthrough pins 301 and 340, a capsule 302 having a cavity 308 therein, a transducer 304, and conductors 328 and 330 (e.g., electrically-conductive ribbon, wire, metallic tab). The transducer 304 may be a sensor, such as a pressure sensor, an optical sensor, a biochemical sensor, a protein sensor, a motion sensor (e.g., an accelerometer or a gyroscope), a temperature sensor, a chemical sensor (e.g., a pH sensor), a genetic sensor, and the like. In some embodiments, the transducer 304 may be a sensing transducer, an actuating transducer, an IC-only transducer, or combinations thereof, or other suitable transducers. Examples of sensing transducers include a sensor and an integrated circuit integrated on a chip (e.g., a silicon substrate or micro-electromechanical system (MEMS) device or nano-electro-mechanical system (NEMS) device), a sensor element without an integrated circuit built into a substrate (e.g., glass, ceramic, silicon, or other suitable material), and a sensor element built into a substrate with an integrated circuit hermetically encapsulated or packaged into a substrate. Examples of actuating transducers include an actuator and an integrated circuit integrated on a chip (e.g., a silicon substrate or MEMS device or NEMS device), a actuator element without an integrated circuit built into a substrate (e.g., glass, ceramic, silicon, or other suitable material), and an actuator element built into a substrate with an integrated circuit hermetically encapsulated or packaged into a substrate. Such actuating transducers may include a piezoelectric element actuator for vibration. Examples of IC-only transducers include an integrated circuit on a silicon substrate (e.g., an IC-logic multiplexer on a lead or a memory chip for sensor calibration coefficients) and an integrated circuit hermetically encapsulated or packaged into a substrate (e.g., glass, ceramic, silicon, or other suitable material).

Components of the transducer module 300 may be able to communicate electrically. The feedthrough pins 301 and 340 may extend into the cavity 308, and the transducer 304 may be positioned within the cavity 308. In some embodiments, the transducer 304 may be disposed on a lead and not within the cavity 308. Allowing the transducer 304 to be exposed to various media, allows for easier and more cost-effective manufacturing of transducer modules and potential space savings without sacrificing the quality of assemblies having hermetically-sealed capsules. The feedthrough pin 301 may be insulated from capsule 302 by means of an insulative ferrule 322 (e.g. glass, plastic, etc.) that is provided through an end wall 312 of the capsule 302. The capsule 302, the ferrule 322, and the feedthrough pin 301 may provide a rigid structure, whether formed integrally or formed separately and subsequently assembled. The second feedthrough pin 340 may be provided through an opposite end wall 310 of the capsule 302 in a similar manner. In some embodiments (e.g., distal-tipped sensors or actuators), the second feedthrough pin 340 may be provided through the same end wall 312 of the capsule 302. The feedthrough pins 301 and 340 may be electrically coupled to the wire conductor coils 202 and 204 shown in FIG. 2, allowing the transducer 304 to transmit signals representative of pressure to, e.g., an IMD. Referring again to FIG. 3, the capsule 302 may be formed of any suitable biocompatible material, such as titanium, or a biocompatible polymer. The capsule 302 may take any suitable shape, such as an elongated tube or any other suitable configuration.

In some embodiments, the transducer 304 may include an integrated circuit 314. In some embodiments, the integrated circuit 314 may be supported by a substrate. A substrate is a body or a base layer onto which other layers are deposited to form a circuit. Ideally, the substrate is bare silicon with protection of an active side and corrosion-resistant pads to which connections may be made. The integrated circuit, optionally formed on the substrate, may be an active device or a passive device. An active device periodically monitors some characteristic (e.g. voltage, current etc.), delivers therapy, or generates an output. A passive device, in contrast, is dormant until acted upon by a stimulus (e.g. mechanical stress, a radio frequency query, etc.). A substrate may be a sensor such as a transducer. Transducers include, for example, pressure sensors, accelerometers, and other suitable devices that convert mechanical inputs to electrical signals.

In other embodiments, the substrate may be made of glass, alumina, ceramic, or other suitable material. In such embodiments, the substrate may perform a sensing function, and the integrated circuit 314 may perform a processing function. The integrated circuit 314 may be configured to convert sensed phenomena into representative electrical signals.

The transducer 304 may sense phenomena in a variety of ways. For example, the transducer 304 may include a flexible diaphragm that, when subjected to fluid pressure, may create a capacitance with a nearby fixed plate. In another example, the transducer 304 may include piezoelectric material that creates an electrical signal when subjected to a force due to surrounding fluid pressure.

The transducer 304 may be configured to provide information to, e.g., an IMD. Such information may be in the form of signals representative of sensed phenomena. In some embodiments, the transducer 304 may be subjected to an AC bias. In some embodiments, the transducer 304 may be subjected to a DC bias. In some embodiments, the transducer 304 may be subjected to combination AC and DC bias. The transducer 304 may be electrically coupled to feedthrough pins 301 and 340 by means of flexible conductors 328 and 330, respectively (e.g., wires, ribbons, or other metallic tabs made of materials such as titanium, niobium, tantalum, platinum, or alloy thereof). Exemplary interconnects between the conductors 328 and 330 and the transducer 304 are discussed in greater detail below.

In some embodiments, the transducer 304 may be effectively suspended within cavity 308, being coupled only to the conductors 328 and 330 and not in any other way to the capsule 302. In this way, forces that are exerted on the feedthrough pins 301 and 340 may be transferred to the capsule 302 and not to the transducer 304. These strain relief characteristics are described in greater detail in commonly assigned U.S. patent application Ser. No. 11/096,150, entitled "Monolithic Integrated Circuit/Pressure Sensor on Pacing Lead," which is incorporated by reference herein in relevant part.

In some embodiments, the interconnect may be exposed to various types of media. For example, an interconnect allowing a MEMS/IC-type sensor to communicate with an IMD may be exposed to different biological fluids. Some of the biological fluids could tend to disrupt the electrical connections between the sensor and the IMD.

Figure 4:
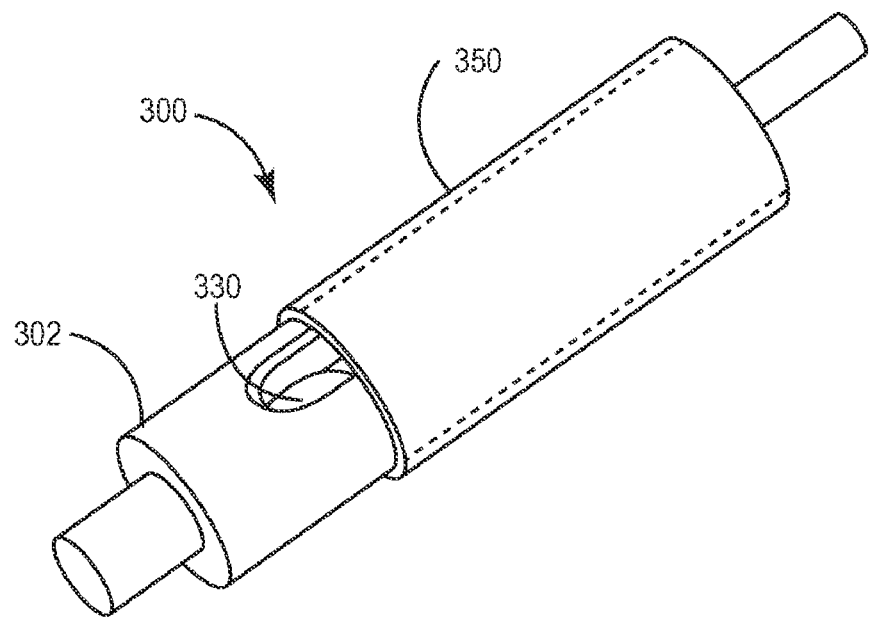
FIG. 4 is a perspective view of the transducer module of FIG. 3 including a sheath.

FIG. 4 shows the transducer module 300 with a sheath 350. The sheath 350 may surround the capsule 302. The sheath 350 may be semi-permeable. The sheath 350 may be made of polyurethane, silicone, or other similar material. The transducer module 300 may be coated. The coating may be an atomic-layer-deposition laminate, silicone, polyurethane, glasses, ceramics, combinations thereof, and/or other similar coatings. A potting may be applied over the interconnect between the conductors 328 and 330 and the transducer 304.

Figure 5:
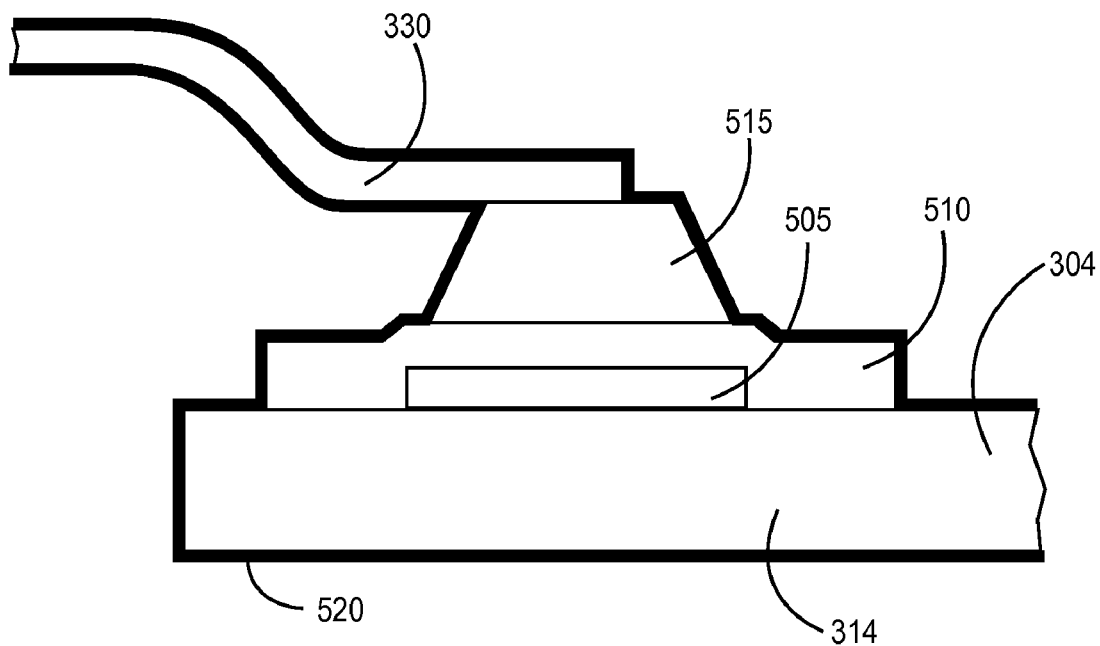
FIGS. 5-8 are side views of exemplary interconnects between a conductor and a sensor.

FIG. 5 shows a closer view of an exemplary interconnect between one of the conductors 330 and the transducer 304 of FIG. 3. Referring again to FIG. 5, the transducer 304 may include the integrated circuit 314 and a pad 505. In some embodiments, the transducer 304 may not include an integrated circuit 314. In such embodiments, the interconnect may connect the conductor 330 directly to the transducer 304 (e.g., for capacitor-type sensors, the conductor 330 may connect directly to the capacitor). In embodiments including the integrated circuit 314, the pad 505 may provide an interconnect between the integrated circuit 314 and other components. The pad 505 may be made of aluminum, titanium, platinum, or other suitable electrically-conductive materials. In some embodiments, the pad 505 may be fabricated through a standard 3 μm fabrication process. In some embodiments, the pad 505 may have a thickness of approximately 0.5-1 μm.

Attaching the conductor 330 directly to the pad 505 may prove difficult (e.g., because they may be made of different materials, because the pad 505 may be too small to provide a welding surface, because they may be unable to handle the requisite thermal loads). Steps may be taken to provide for effective attachment. The transducer 304 may include a first layer 510. The first layer 510 may be made of titanium, niobium, tantalum, vanadium, hafnium, zirconium, or alloy thereof, or other suitable material. Such materials may form a stable low temperature surface oxide layer, which may provide a stable low corrosion rate pad under DC bias and saline exposure (e.g., body fluids). The first layer 510 may be applied by sputtering, cold/thermal spraying, electro-deposition, electroless deposition, or other suitable deposition technique. In some embodiments, the first layer 510 may be approximately 1 μm thick.

In some embodiments, the transducer 304 may include a second layer 515. The second layer 515 and the first layer 510 may be made of similar materials. The second layer 515 may be applied by any deposition technique discussed herein or by any suitable deposition technique. In some embodiments, the second layer 515 may be greater than about 25 μm thick. When viewed from the side, the layers 510, 515 may be stepped or tiered (i.e., a stair pattern), may have a gradual slope, may have a combination profile, or may have some other suitable profile. The shape of the combined first layer 510 and second layer 515 may be circular (e.g., with a nominal diameter of approximately 0.020 inches), rectangular, hexagonal, or other suitable shapes. The second layer 515 may provide a platform to which the conductor 330 may be attached using standard techniques (e.g., laser welding, resistance welding, etc.). The platform to which the conductor 330 may be attached may comprise a greater or lesser number of layers having a variety of thicknesses and made from a variety of materials. In some embodiments, a feedthrough (see, for example, feedthrough 340 of FIG. 3) may be attached directly to the platform. The platform may serve as a thermal sink, dissipating a portion of the heat generated through some attachment techniques. As is discussed above, the conductor 330 and the transducer 304 may be coated with a coating 520.

Embodiments similar to that shown in FIG. 5 may reduce stresses existing between the pad 505 and the transducer 304. When the pad 505 is deposited on the transducer 304, the pad 505 may exert either a tensile force or a compressive force on the transducer 304, depending on the deposition technique used, the process parameters, the geometry of the pad 505, the material of the transducer 304, the material of the pad 505, the post-processing parameters, and other factors. Such force may cause damage to the transducer 304, such as cracking. The first layer 510 and/or the second layer 515 may serve to reduce such force. For example, if the pad 505 is exerting a tensile force on the transducer 304, the first layer 510 may be deposited in such a way as to exert a compressive force on the pad 505, thereby reducing (or possibly eliminating) the magnitude of the tensile force the pad 505 may exert on the transducer 304.

In the example of the preceding paragraph, the first layer 510 could exert a compressive force on the pad 505 that is significantly greater in magnitude than the tensile force exerted by the pad 505 on the transducer 304. In such instances, the compressive force could cause damage to the transducer 304. The second layer 515 may be deposited to exert a tensile force on the first layer 510. The combination of layers may serve to balance forces, resulting in a minimal amount of force being exerted on the transducer 304. It should be understood that a greater or lesser number of layers, having a variety of thicknesses, and made from a variety of materials, may be implemented to achieve the desired stress reduction.

In some embodiments, the transducer 304 may include a pad and a matrix that is positioned over the pad. In such embodiments, the matrix may have interstitial air. The matrix may be made of metal or other electrically conductive material. The matrix may be applied by any of the deposition techniques discussed herein or by any other suitable deposition technique. In some embodiments, the matrix may serve to reduce stresses to the transducer 304. In embodiments in which a conductor is welded to the matrix, the matrix may transfer only a minimal amount of the corresponding thermal load to the transducer 304.

Figure 6:
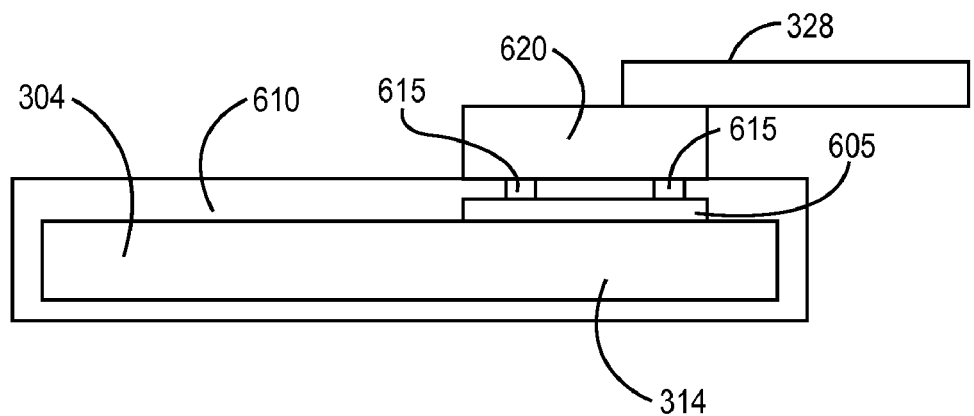

FIG. 6 shows a closer view of an exemplary interconnect between one of the conductors 328 and the transducer 304. The transducer 304 may include a pad 605, which may provide an interconnect between the transducer 304 and other components. The pad 605 may be similar to the pad discussed in connection with FIG. 5.

Referring again to FIG. 6, an interlayer 610 may be applied over the pad 605. The interlayer 610 may be parylene, polyimide, silicone (e.g., in an embodiment having a glass or ceramic substrate), a polymer, or other suitable material. The interlayer 610 may be approximately between 7 and 40 μm thick. The interlayer 610 may be applied by spin coating, spray coating, vacuum deposition, vapor deposition, or other suitable application technique.

Vias 615 may extend through the interlayer 610 to allow the pad 605, and thus the transducer 304, to communicate with other components. The vias 615 may be laser or chemically etched, or may be provided by other suitable means. The vias 615 may be made of an electrically-conductive material.

An upper pad 620 may be positioned on top of the interlayer 610. The upper pad 620 may be made of tantalum, niobium, titanium, or other similar electrically conductive material. In certain embodiments, the upper pad 620 may be approximately 25-80 μm thick. The upper pad 620 may have characteristics similar to that of the combined layers discussed in connection with FIG. 5. Referring again to FIG. 6, the upper pad 620 may provide a platform to which the conductor 328 may be attached, such as by parallel gap welding, laser ribbon bonding, or other welding/attaching techniques. This platform may have one or more characteristics of the platform discussed in connection with FIG. 5. Embodiments similar to that shown in FIG. 6 may provide additional mechanical support, thereby isolating strains exerted on the upper pad 620 and preventing such strains from being transferred to the transducer 304 in a manner similar to that discussed in connection with FIG. 5.

Figure 7:
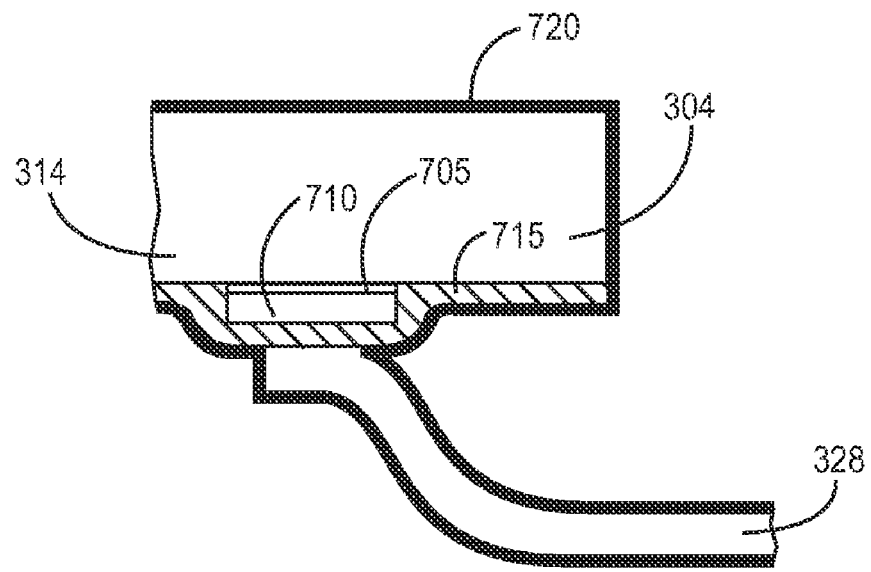

FIG. 7 shows a closer view of an exemplary interconnect between one of the conductors 328 and the transducer 304. FIG. 7 illustrates that the interconnect may be located on either side of the transducer 304. Indeed, the terms "over," "on top of," or other similar terms are used herein to refer to a side of an object that is opposite the transducer. So, for example, in the preceding paragraph, the "upper pad 620 may be positioned" on the side of the "interlayer 610" that is opposite the transducer 304. Accordingly, the interconnect may be located on either side of the transducer 304.

Referring again to FIG. 7, the transducer 304 may include a pad 705. The pad 705 may be similar to the pads discussed elsewhere herein. The transducer 304 may include a stud 710. The stud 710 may be made of any suitable electrically-conductive material, such as materials discussed herein. The stud 710 may be fabricated by ordinary machining processes. The stud 710 may be a thick refractory metal. In some embodiments, the stud 710 may communicate directly with the transducer 304, without the need of the pad 705. A conductive layer 715 may be deposited over the stud 715. The conductive layer 715 may secure the stud 710 in position. The conductive layer 715 may be made of any of the electrically-conductive materials discussed herein. The conductive layer 715 may provide a platform to which the conductor 328 may be attached using any of the techniques discussed herein. This platform may have one or more characteristics of the platform discussed in connection with FIG. 5. Embodiments similar to that shown in FIG. 7 may provide strain relief in a manner similar to that discussed in connection with FIG. 5. As is discussed above, the conductor 330 and the transducer 304 may be coated with a coating 720.

Figure 8:
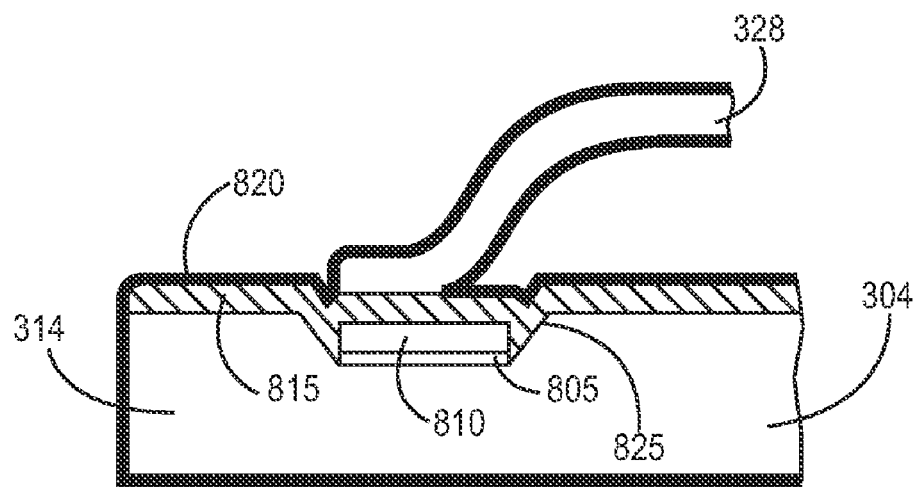

FIG. 8 shows a closer view of an exemplary interconnect between one of the conductors 328 and the transducer 304. The embodiment of FIG. 8 may be similar to that of FIG. 7 in that the embodiment of FIG. 8 may include a pad 805, a stud 810, a conductive layer 815, and a coating 820. In some embodiments, the transducer 304 may include a trench 825 into which the pad 805 and/or the stud 810 may be positioned. In such embodiments, the additional height introduced by the stud 810 may be minimized, thereby saving valuable space.

Embodiments similar to those shown in FIGS. 5-8 may provide for improved accommodation of the transducer 304 being subject to a DC bias. While previous interconnects have encountered problems (e.g., corrosion, etc.) under DC bias conditions, one or more of the interconnects discussed herein may overcome those problems. The robust connection between conductors and transducers of some of the embodiments discussed herein may operate properly under DC bias conditions.

Although the exemplary interconnects between a conductor and a transducer shown in FIGS. 5-8 have been discussed in connection with IMDs, such interconnects may be useful in other environments, such as automotive, salt water, chemical, petroleum instrumentation, or other similar environments.

For nonhermetic sensors associated with implantable medical devices, it is desirable that the contact pads that are electrically connected with conductor 330 be compatible with the in vivo environment. Typically, the contact pad thickness (e.g. 25-100 microns etc.) is significantly greater than typically found in semiconductor applications. Such pad thicknesses can develop stress through thermal excursions that may affect the underlying substrate. The claimed invention provides biocompatible contact that can be welded or otherwise joined and has a coefficient of thermal expansion (CTE) that can be tailored to match the substrate such as silicon or silica. The metallization may also have application outside the medical field for example in MEMS devices in harsh environments.

Figure 9:
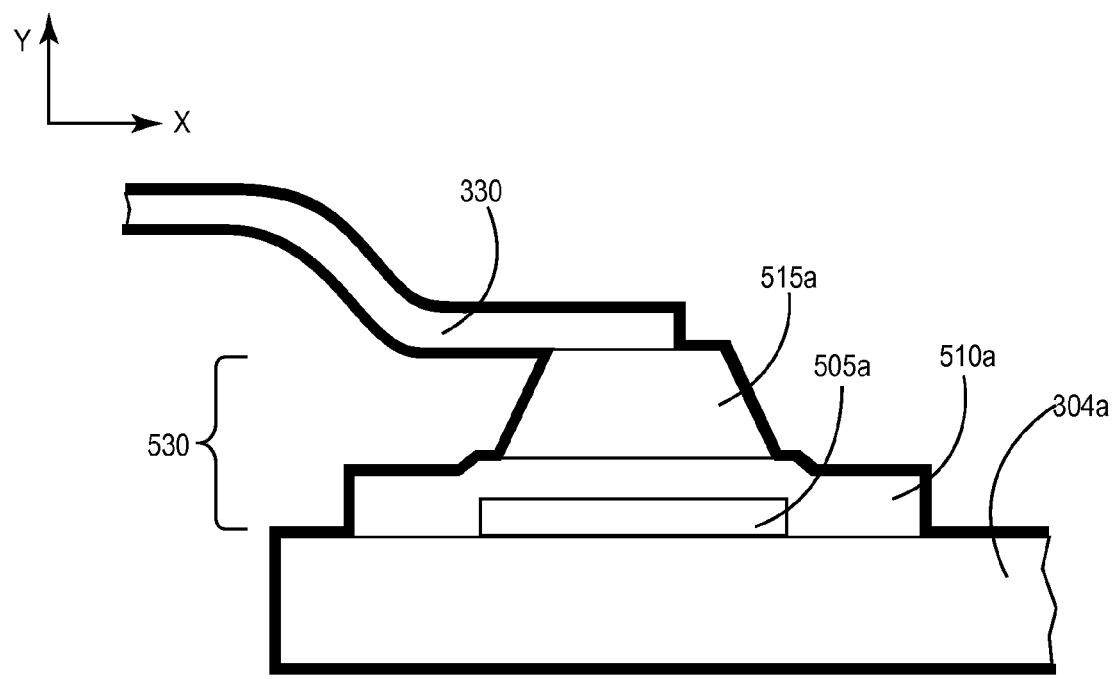
FIG. 9 is a cross-sectional view of another exemplary interconnect between a conductor and a sensor.

FIG. 9 depicts an enlarged view of an exemplary interconnect 530 between one of the conductors 330 and substrate 304a. Interconnect 530 is a corrosion-resistant, biocompatible metallization that significantly reduces the cross-sectional width (along the y-axis) of implantable sensors. Interconnect 530 may be used for all types of sensors, smart leads or other suitable devices.

Interconnect 530 comprises first layer 510a, pad 505a, and second layer 515a. In one embodiment, at least one or all of pad 505a, first layer 510a, and second layer 515 may comprise a material that exhibits a negative CTE. A negative CTE is defined as a material that contracts when exposed to heat. Heat is typically generated during one of the processes (e.g. parallel gap welding, laser ribbon bonding etc.) used to join a conductor 330 to pad 505a. Niobium pentoxide ($Nb_2O_5$), an insulator, is an exemplary material that possesses a negative CTE. In one embodiment, a composite of niobium (Nb) and $Nb_2O_5$ is used to form one or all of pad 505a, first layer 510a, and second layer 515a. A variety of composite materials can be made by varying the ratio of Nb to $Nb_2O_5$.

Presented below is an exemplary calculation to determine an optimal CTE for each component of a composite material relative to a substrate. The CTE of a composite material is equal to the sum of the products of the volume fraction of each component or constituent multiplied by its CTE. To illustrate, consider the composite material (designated as C) that comprises two constituents A and B, where:

$X$=volume fraction of A, $1-x$=volume fraction of B, $CTE_A$=CTE of A, $CTE_B$=CTE of B, $CTE_C$=CTE of C, and $X*CTE_A+(1-X)*CTE_B=CTE_C$.

Constituent includes an element, a compound, an alloy, or any combination thereof.

Using the values of 7.3 parts per million (ppm)/centigrade (° C.) for the CTE of Nb, and 2 ppm/° C. for the CTE of $Nb_2O_5$, a 50/50 volumetric ratio composite material about matches the CTE of a substrate such as silicon (2.6 ppm/° C.). A 27/73 ratio (Nb/$Nb_2O_5$) produces a composite material CTE of about 0.5 ppm/° C. to match fused silica. Skilled artisans appreciate that numerous other ratio combinations of Nb and $Nb_2O_5$ may be implemented. For example, Nb may range from 10 to 40 percent whereas $Nb_2O_5$ may range from 60% to 90%.

Table 1 lists a variety of embodiments that may be implemented; however, skilled artisans appreciate that numerous other embodiments of the claimed invention. Since CTE is a function of temperature, the target values for the CTE may be different based on the temperature range of interest when joining, for example, a conductor 330 to pad 505a. Embodiment 1 lists a substrate such as silicon that has a CTE of 2.6 while the volumetric ratio of $Nb/Nb_2O_5$ is about 49/51. Embodiment 2 lists silicon dioxide as the substrate which has a CTE of 2.6 while the volumetric ratio of $Nb/Nb_2O_5$ is about 27/73. Embodiment 3 lists borosilicate glass as the substrate which has a CTE of 4 while the volumetric ratio of $Nb/Nb_2O_5$ is about 65/35. Embodiment 4 lists silicon nitride as the substrate which has a CTE of 3.6 while the volumetric ratio of $Nb/Nb_2O_5$ is about 60/40. Embodiment 5 lists silicon carbide as the substrate which has a CTE that ranges from about 2.2 to about 4.5 while the volumetric ratio of $Nb/Nb_2O_5$ ranges from about 45/55 to about 70/30. Embodiment 6 lists zinc oxide (ZnO) as the substrate which has a CTE that ranges from about 5.0 to about 8.0 while the volumetric ratio of $Nb/Nb_2O_5$ ranges from about 45/55 to about 75/25.

TABLE 1

Exemplary CTEs for a variety of substrates

| Embodiment | Substrate | CTE (ppm/° C.) | Volumetric ratio of $Nb/Nb_2O_5$ |
|---|---|---|---|
| 1 | Silicon | 2.6 | 49/51 |
| 2 | Silicon dioxide (SiO2) | 0.5 | 27/73 |
| 3 | borosilicate glass | 4 | 65/35 |
| 4 | Silicon nitride (SiN) | 3.6 | 60/40 |
| 5 | Silicon carbide (SiC) | 2.2–4.5 | 45/55–70/30 |
| 6 | Zinc oxide (ZnO) | 5.0–8.0 | 75/25 |

Co-deposition (e.g. sprayed, sputtered etc.) of Nb and $Nb_2O_5$ can be performed simultaneously without using vias in order to make electrical connections in interconnect. In one embodiment, Nb and $Nb_2O_5$ are premixed and then introduced as a single feed stream. In another embodiment, Nb and $Nb_2O_5$ are each introduced as separate feed streams. The Nb and/or $Nb_2O_5$ could also be deposited in alternating layers with vias to establish electrical connection through the $Nb_2O_5$ layers (since $Nb_2O_5$ is an insulator).

Numerous methods may be used to introduce Nb and/or $Nb_2O_5$ over a substrate or other surface. Exemplary methods for introducing Nb and/or $Nb_2O_5$ over a substrate or other surface include e-beam evaporation, sputtering, thermal spray and other suitable methods. Thermal spray generally describes several coating methods such as flame spray, electric arc, plasma arc, vacuum plasma, cold spray, high velocity oxyfuel and others. It may also be possible to formulate thick film pastes that can be printed and fired or laser sintered to form the interconnect 530. The metal can be deposited in a thin layer (e.g. a few microns (e.g. 5 or 10 microns)) or in thicknesses of several millimeters. Interconnect 530 is compatible with a variety of joining methods including resistance welding and laser welding. The CTE can be uniform or varied to achieve the desired result. For example, if Nb is being joined with glass, the pad could have a low CTE. Therefore, it may be desirable to select a constituent or composite that exhibits a CTE that more closely matches the joining element than the CTE associated with the substrate. This metallization technique mitigates high stress associated with relatively thick metallization on such substrates as silicon, fused silica, etc.

Figure 10:
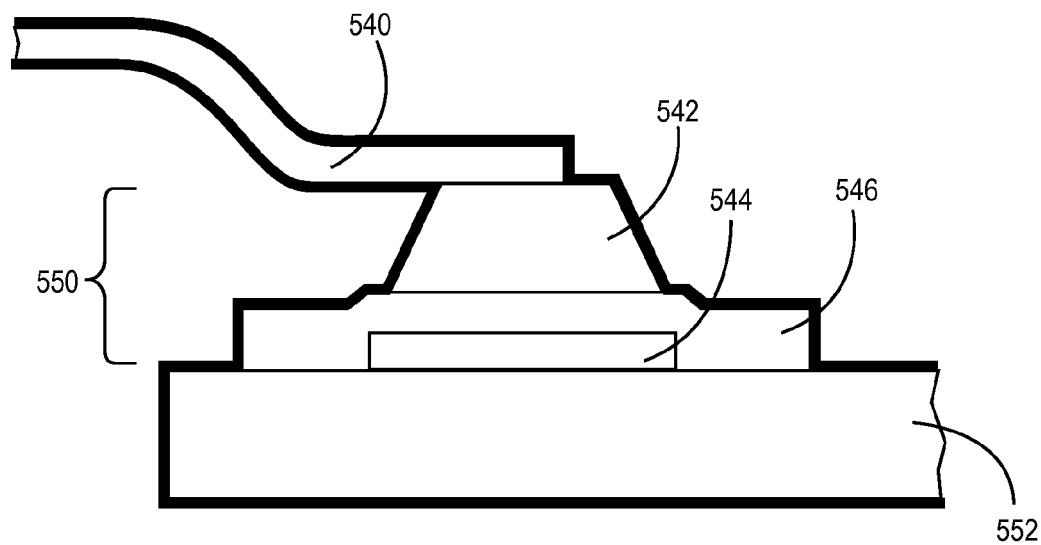
FIG. 10 is a cross-sectional view of yet another exemplary interconnect between a conductor and a sensor.

FIG. 10 depicts an enlarged view of another exemplary conductive interconnect 550 between conductive element 540 (e.g. conductor etc.) and or substrate 552. Substrate 552 is a body or a base layer onto which other layers are deposited to form a circuit. Ideally, substrate 552 is bare silicon with protection of an active side and corrosion-resistant pads to which connections may be made. The integrated circuit, optionally formed on substrate 552, may be an active device or a passive device. An active device periodically monitors some characteristic (e.g. voltage, current etc.), deliver's therapy, or generates an output. A passive device, in contrast, is dormant until acted upon by a stimulus (e.g. mechanical stress, a radio frequency query, etc.). Substrate 552 may be a sensor such as a transducer. Transducers include, for example, pressure sensors, accelerometers, and other suitable devices that convert mechanical inputs to electrical signals.

Interconnect 550 comprises first layer 546, conductive element 544, and second layer 542. In one embodiment, at least one or all of pad 544, first layer 546, and second layer 515 may comprise a material that exhibits a negative CTE. A negative CTE is defined as a material that contracts when exposed to heat. Heat is typically generated during one of the processes (e.g. parallel gap welding, laser ribbon bonding etc.) used to join a conductor 330 to pad 544. $Nb_2O_5$, an insulator, is an exemplary material that possesses a negative CTE. In one embodiment, a composite of Nb and $Nb_2O_5$ is used to form one or all of pad 544, first layer 546, and second layer 542. A variety of composite materials can be made by varying the ratio of Nb to $Nb_2O_5$.

FIGS. 11-13 depict a variety of other embodiments related to corrosion resistant interconnects that may be used to connect conductor 330 to pad 505a (FIG. 9). In one embodiment, each element of interconnect 550 such as first layer 546, pad 505a, and second layer 515a may be formed of at least one of the embodiments depicted in FIGS. 11-13. In another embodiment, first layer 546, pad 505a, and second layer 515a comprise the same interconnect layers selected from one of the embodiments depicted in FIGS. 11-13. In another embodiment, at least one of first layer 546, pad 505a, and second layer 515a comprises a different embodiment depicted in FIGS. 11-13 than one of the other elements that comprise interconnect 530.

Referring to FIG. 11, interconnect 600 comprises first, second, third and fourth layers 602, 604, 606, and 608, respectively. First, second, and third layers 602, 604, 606 respectively are each about 15-30 microns thick. Fourth layer 608 is about 5-10 microns thick. First layer 602 may comprise Ti-45% Nb, Ti, or Nb. Second layer 604 comprises Nb. Third layer 606 comprises Ti-45% Nb. Fourth layer 608 comprises Ti.

Referring to FIG. 12, interconnect 700 comprises first, second, third, fourth fifth, and sixth layers 702, 704, 707, 708, 710, and 712, respectively. Interconnect 700 is about 25-100 microns thick. First, second, and third layers are each about 15-30 microns thick. Fourth layer is about 5-10 microns thick. First layer 702 may comprise Ti-45% Nb, Ti, or Nb. Third, and fifth layers 706, 710 comprise Ti-45% Nb. Second and fourth layers 704, 708 comprise Nb. Sixth layer 712 comprises Ti.

Referring to FIG. 13, interconnect 800 comprises first, second, third, fourth fifth, sixth, seventh, eight, ninth, and tenth layers 802, 804, 807, 808, 810, 812, 814, 816, 818, and 820, respectively. Interconnect 800 is about 25-100 microns thick. First, second, and third layers are each about 15-30 microns thick. Fourth layer is about 5-10 microns thick. First layer 802 may comprise Ti-45% Nb, Ti, or Nb. Third, fifth, seventh, and ninth layers 802, 806, 810, 814 and 818, respectively, comprise Ti-45% Nb. Second, fourth, sixth, and eighth layers 804, 808, 812, 816 respectively, comprise Nb. Tenth layer 820 comprises Ti.

Skilled artisans appreciate that various interconnects may be made that are similar to the embodiments depicted in FIGS. 11-13. Individual layer and total thicknesses are optimized based on the application. The underlying basis for the stack-up with alternating layers of high and low thermal conductivities is to minimize the thermal shock of the underlying substrate due to welding to the pad. High thermal conductivity layers allow for lateral heat spreading while the low thermal conductivity layers slow the heat transfer to the substrate.

Not shown, but also possible are electrically insulating materials that could be layered with vias or other openings allowing electrical contact through them. Silicon has high thermal conductivity and low coefficient of thermal expansion and may also be useful. The silicon would probably be deposited as polysilicon which has poorer corrosion resistance than single crystal silicon and should therefore be covered completely by more corrosion-resistant material(s).

Thus, embodiments of media-exposed interconnects transducers are disclosed. One skilled in the art will appreciate that the media-exposed interconnects for transducers can be practiced with embodiments other than those disclosed. Moreover, it should be understood that the features of the disclosed embodiments may be used in a variety of combinations. For example, the embodiments described herein may be used in smart leads. Smart leads may have three or four conductors from the device (e.g. neurological devices etc.) and then near the distal end of the lead be multiplexed to the various delivery locations. This is a concept that has particular application for neurological devices that provide stimulation at various sites along a lead. The embodiment in FIG. 9 is substantially similar to FIGS. 5-8. Additionally, the embodiment depicted in FIG. 9 could be part of a lead assembly as shown in FIGS. 1-4, an untethered device or other suitable device.

The combinations of features of the disclosed embodiments are compiled only for purposes of illustration and not limitation. The present invention is limited only by the claims that follow.

What is claimed is:

1. An interconnect for an implantable medical device comprising:
    a pad; and
    a first layer introduced over the pad, wherein one of the pad and the first layer comprise a negative coefficient of thermal expansion material comprising niobium pentoxide ($Nb_2O_5$);
    wherein one of the pad and the first layer comprises a range of 25 to 75 of Nb and 75 to 25 of $Nb_2O_5$ in a $Nb/Nb_2O_5$ ratio.

2. The interconnect of claim 1, wherein one of the pad and the first layer comprises 27/73 $Nb/Nb_2O_5$ ratio.

3. The interconnect of claim 1, wherein the coefficient of thermal expansion ranges from 0.5 to 8.0.

4. A joint in an implantable medical device comprising:
    a substrate;
    a conductor;
    an interconnect coupled to the substrate and to the conductor, the interconnect comprising:
        a pad; and
        a first layer introduced over the pad, wherein one of the pad and the first layer comprises a negative coefficient of thermal expansion material;
        wherein one of the pad and the first layer comprises a range of 25 to 75 of Nb and 75 to 25 of $Nb_2O_5$ in a $Nb/Nb_2O_5$ ratio.

5. The joint in an implantable medical device of claim 4, wherein the substrate comprises one of silicon, silicon dioxide, borosilicate glass, silicon nitride, silicon nitride, silicon carbide, and zinc oxide.

6. A joint in an implantable medical device comprising:
    a first element;
    a second element;
    an interconnect coupled to the first and the second elements, the interconnect comprising:
        a pad; and
        a first layer introduced over the pad, wherein one of the pad and the first layer comprises a negative coefficient of thermal expansion material;
        wherein one of the pad and the first layer comprises a range of 25 to 75 of Nb and 75 to 25 of $Nb_2O_5$ in a $Nb/Nb_2O_5$ ratio.

7. The joint in an implantable medical device of claim 6, wherein the first element comprises a substrate.

8. The joint in an implantable medical device of claim 7, wherein the first element comprises one of silicon, silicon dioxide, borosilicate glass, silicon nitride, silicon nitride, silicon carbide, and zinc oxide.

9. The joint in an implantable medical device of claim 6, wherein the coefficient of thermal expansion ranges from 0.5 to 8.0.

10. A joint in an implantable medical device comprising:
    a first element;
    a second element;
    an interconnect coupled to the first and the second elements, the interconnect comprising:
        a pad; and
        a first layer introduced over the pad, wherein one of the pad and the first layer comprises a negative coefficient of thermal expansion material;
    wherein the joint is used to connect a sensor and a conductor; and
    wherein the sensor being one of a pressure sensor, an optical sensor, a biochemical sensor, a protein sensor, a motion sensor, a temperature sensor, a chemical sensor, and a genetic sensor.

* * * * *